United States Patent [19]

Calderwood

[11] Patent Number: 4,978,506
[45] Date of Patent: Dec. 18, 1990

[54] CORROSION PRODUCT MONITORING METHOD AND SYSTEM

[75] Inventor: Andrew S. Calderwood, Forest Hills Boro, Pa.

[73] Assignee: Westinghouse Electric Corp., Pittsburgh, Pa.

[21] Appl. No.: 195,311

[22] Filed: May 18, 1988

[51] Int. Cl.$^5$ .................. G01N 30/00; B01D 36/00
[52] U.S. Cl. .................. 422/73; 73/863.23; 210/263; 210/265; 210/295; 422/68.1; 422/81; 422/101; 436/38; 436/52; 436/177; 436/178; 436/6
[58] Field of Search .................. 422/68, 62, 73, 81, 422/101, 68.1; 436/38, 6, 52, 177, 178; 73/863.23; 210/196, 255, 263, 265, 295

[56] References Cited

U.S. PATENT DOCUMENTS

| | | | |
|---|---|---|---|
| 3,368,385 | 2/1968 | Harvey, Jr. | 73/33.1 |
| 3,976,541 | 2/1976 | Stiteler et al. | 176/37 |
| 4,020,676 | 5/1977 | Nuxhall et al. | 210/196 X |
| 4,050,638 | 9/1977 | Ito et al. | 241/222 |
| 4,207,922 | 6/1980 | Andrieux et al. | 137/625.11 |
| 4,385,113 | 5/1983 | Chapelle et al. | 422/52 X |
| 4,438,649 | 3/1984 | Gilman | 73/432 R |
| 4,446,097 | 5/1984 | Calabrese | 376/256 |
| 4,472,354 | 9/1984 | Passell et al. | 422/62 |
| 4,472,355 | 9/1984 | Hickam et al. | 436/38 X |
| 4,622,306 | 11/1986 | Diive | 436/38 X |
| 4,654,187 | 3/1987 | Fejes | 376/245 |
| 4,765,963 | 8/1988 | Mukogawa et al. | 422/68 |
| 4,766,550 | 8/1988 | Byers et al. | 422/62 X |
| 4,822,744 | 4/1989 | Bellows | 422/68 X |

OTHER PUBLICATIONS

Enka Microdyne Brochure, publication date unknown.
Solomon, Y.; ed. EPRI NP-3402-SR, "Proceedings: Workshop on Corrosion Product Sampling from Hot Water Systems", Mar. 1984.
Sawochka, S. G.; Copley, S. E.; Pearl, W. L.; EPRI NP-2149, "Corrosion Product Transport in PWR Secondary Systems", Dec. 1981.

Sturla, P.; EPRI CS-4950, p. 22-1, Proc. 1985 Symp. Fossil Plant Chemistry.

(List continued on next page.)

*Primary Examiner*—Robert J. Warden
*Assistant Examiner*—Jill Johnston

[57] ABSTRACT

A corrosion product monitoring system and method are described using a recirculation loop including a sample line, a particulate collection vessel, a recirculating pump, a microporous membrane "cross-flow" filter, and valves to control the flow rate and pressure of a fluid sample taken from the secondary fluid system of a nuclear power plant. The liquid sample is processed at a constant flow rate and temperature. When a relatively short time has elapsed in a trial sample run to stabilize conditions in the sample line, an actual sample run is started by feeding sample into the loop. Non-soluble, particulate concentration increases in the filter and particulate collection vessel as the run progresses. The permeate of soluble contaminants is passed through an ion exchange column to concentrate soluble ions in the sample. The filter is backwashed on a timed cycle by filtered water pressurized by a pump, or gas pressure, by realigning the system valves. A total sample volume is determined by measuring the amount of filtered, deionized water discharged during the actual sample run, based on total weight, total flow or time at a constant discharge rate. A concentration factor can be determined from the total sample volume divided by the initial system volume. A sample of the non-soluble particulates can also be drawn from the particulate collection vessel for analysis. The related method includes the steps of: taking a sample from a fluid system; introducing the sample to a recirculation loop having an initial system volume; separating non-soluble particulates from soluble contaminants; suspending the solid particulates; collecting the solid particulates in a particulate collection vessel; and determining a corrosion concentration factor from the total sample volume divided by the initial system volume.

13 Claims, 2 Drawing Sheets

OTHER PUBLICATIONS

Roesmer, J.; SGTD-5.1.1-6053, Feb. 17, 1986; "High pH Chemistry in USA Plants"; EPRI Seminar on PWR Water Chemistry and Radiation Field Control, Mar. 1986.

Penfold, D.; Harrison G. S.; Gill, G. M.; Greene, J. C.; Walker, M. A.; Nuclear Energy, vol. 25, #5, p. 257, 1986.

Chow, W.; Maddalone, R.; Power Eng. vol. 91, #6, p. 42 Jun. 1987.

Moffett, J. W.; Zoski, J. E.; Proc. 39th. Int. Water Conf. p. 371, 1978.

ASTM D-19.11; Power Plant Water Analysis Manual, ch. 46, 1984.

Sundberg, L. L.; EPRI-3402-SR, p. 18-1, Mar. 1984.

Noe, M.; Beslu, P.; Anthoni, S.; Frejaville, G.; EPRI-3402-SR, , p. 3-1, Mar. 1984.

Davis, J.; EPRI-3402-SR, p. 9-1, Mar. 1984.

Moes, H.; Chemical Processing, p. 62, Feb. 1986.

Proposal entitled: "Asco Corrosion Product Transport Characterization and Alternate Hydrogen Monitor Performance Test".

CORROSION PRODUCT SAMPLING SYSTEM

CORROSION PRODUCT SAMPLING SYSTEM

CORROSION PRODUCT MONITORING METHOD AND SYSTEM

BACKGROUND OF THE INVENTION

This invention relates to corrosion monitoring and, more particularly, to a method and system for monitoring corrosion products circulating in the primary or secondary fluid systems of a nuclear power plant.

DESCRIPTION OF THE PRIOR ART

During operation of a nuclear power plant, undesirable corrosion products occur in the primary and secondary fluid systems. Sampling and quantifying these corrosion products is necessary for evaluating the effectiveness of chemistry control programs, which seek to minimize the corrosion of the power plant components, and the transport of the products throughout these systems.

More particularly, the fluid systems must be sampled to develop information concerning the concentration and amounts of solid particulates and soluble corrosion products, and their cumulative deposition or removal from critical components of the power plant. This information is important in the control of activity levels during operation of the primary system, and the control of corrosion in the steam generator and other system components. This information is also needed for evaluating the effects, on corrosion transport, of changes in component materials, the performance of fluid purification systems and plant operational procedures. Finally, this information can be used to estimate the impact of corrosion product transport on system availability, and the benefits of cleanup procedures, plant upgrades, component replacement and improved chemistry control procedures.

Current methods and systems for corrosion product monitoring in power plants have yielded unsatisfactory results. With these methods and systems, it is difficult to establish an accurate relation between monitored corrosion product data and plant conditions, since data scatter can be caused by improper sampling procedures. Integrated sampling over extended periods can improve the data reproducibility. However, transient effects cannot be monitored by integrated sampling. Moreover, integrated sampling is very time and labor-intensive.

Further complicating monitoring efforts are the inherent differences/requirements of the primary and secondary fluid systems, as described below.

In the primary system the major concern is the effect of corrosion product transport on the increase in activity levels caused by the transport and deposition of radioactive corrosion products in the components thereof. Estimates can be made using computer models of the various corrosion and transport processes with kinetic parameters whose values have usually been determined experimentally by loop testing. However, the success of direct measurement of the transport of crud (a very dilute suspension of solid particulate corrosion products) and soluble corrosion products in operating power plants has been limited by sampling problems.

For example, if a corrosion product monitor including a conventional metal filter for sampling particulates and cation exchange columns for concentrating soluble metal ions is used, the filters are easily clogged by fine corrosion products. Furthermore, corrosion of the metal filter material itself affects the accuracy of the weight value of the corrosion products. Corrosion products deposited on filter surfaces can also change by undergoing reactions and recrystallization dependent on the redox potential of the filter material used (cellulose, silver, etc.). Such changes can affect the accuracy of the measurements of the soluble and insoluble metal concentrations, the particle size distribution and the identification of the corrosion product species in the sample.

Moreover, there has recently been considerable interest in operating the reactor coolant system at a higher pH range in an effort to minimize the transport of corrosion products. This interest is based on the assumption that higher pH reduces the suspended crud concentrations in the nuclear reactor coolant to very low levels, on the order of 10 parts per billion (ppb) and minimizes the rate of deposition on the reactor core and the increase in ex-core radiation dose rates. However, successful use of the higher pH condition requires accurate determinations of the transport of both solid particulates and soluble corrosion products. Conventional monitoring methods and systems have not proved adequate for this purpose.

In the secondary system the concern is with the effects of corrosion product transport on components such as the steam generator where corrosion deposition can increase the potential for corrosion attack at critical points. That is, transported corrosion products increase the potential for localized corrosion attack by forming sludge deposits on tube sheets and tube support plates, and scale or copper deposits on heat transfer surfaces. Most of the soluble and insoluble corrosion products transported by the feedwater into the steam generator are not removed by blow down so that concentrations even in the ppb range can cause significant, detrimental deposits over time.

The ineffectiveness of the current methods and systems is underscored by a recent, actual feedwater piping rupture at a nuclear power plant, which could not be detected by conventional monitoring. The operating factors which significantly affect the erosion/corrosion rate in carbon steel feedwater piping are the dissolved oxygen concentration, feedwater pH, flow velocity and temperature. The values of these parameters can vary with each plant's chemistry control at startup, shutdown and normal operating conditions.

It is desirable to perform in-plant tests on the effects of changing chemistry control parameters such as dissolved oxygen concentration, pH additives such as morpholine or another amine, and feedwater oxygen removal by hydrazine or alternative additives, on corrosion product transport rates. The effect on the erosion-corrosion rate could be estimated if the variation in particulate and soluble iron concentrations with increased velocity could be monitored in the affected components. By determining the effects of changes in the control parameters, the optimum chemistry control program for a specific plant can be determined relatively quickly. Operating plants could then take corrective action to avoid pipe ruptures on a plant-specific basis, depending on the particular mix of materials and flow velocities at affected locations in the condensate and feedwater systems.

It is known that the concentration of corrosion products in power plant fluid systems can not be effectively determined simply by conventional direct analysis using in-line monitors or grab sample analysis. Instead, transition metal analysis must be performed by colorimetric analysis or by atomic adsorption spectroscopy with the limits of detection on the order of several ppb. The total concentration of transition metal corrosion products in acidified grab samples under normal operating conditions is close to or less than these limits of detection. As a result, averaging of several samples and statistical analysis are still required to obtain meaningful qualitative results from grab samples. It is also usually the practice to concentrate the sample several hundred times before analysis to obtain the accuracy required for estimating mass balances and cumulative amounts of corrosion products.

Due to the above limitations, the method most often used for obtaining particulate corrosion product samples from power plant feedwater is to pass a 1 liter volume of sample through a metal Millipore® filter holder, typically a 47 mm. diameter, 0.45 micrometer pore size membrane filter. The type and amount of the corrosion product is determined by comparing color tint and intensity of the deposit on the filter membrane with a standard stain. This method is basically a qualitative method and can only be used for hydrated iron oxide or magnetite. The solids collected should be greater than 250 micrograms for accurate results. As a result, this method is only suitable for fairly high corrosion product concentrations. Filtering is followed by ion exchange impregnated filter papers or resin columns for accumulating soluble corrosion products.

Quantitative results at low particulate concentrations, from 0.1 to 10 ppb, can be obtained from the increase in weight of the dried membrane. However, Millipore® filters have soluble contaminants and cannot be dried to a consistent weight. As a result, weighing errors occur on the order of 1 mg. Further, trace metal contamination in the filters is variable and can be around 0.01 mg. iron and 0.002 mg. copper. In addition, prolonged immersion results in increased weight loss by extraction of the polymer base of the membrane, amounting to potentially 10% of the membrane weight.

Similar problems are noted with ion exchange filter papers used to collect soluble metals. To obtain accurate determinations at the ppb level very large volumes of sample must be filtered and, due to the small size of the filter membrane, this method requires several days of sampling.

Integrated sampling using such a filter has been attempted with varying results. Over long periods of sampling, ranging from several hundred to several thousand hours, reasonable estimates of average corrosion product concentrations and transport rates have been obtained and mass balances over system components have been calculated. However, this method is not a true integrated sampling system since the flow rate through the membrane has to be controlled manually as the resistance due to the filter cake increases rapidly. In addition, up to half the corrosion product particles can be smaller than 0.45 microns, so that an appreciable amount of particulate corrosion products can pass through the Millipore® filter and foul the ion exchange sample columns, seriously affecting the accuracy of the results.

As a result of the above-discussed inadequacies of the prior art, corrosion product monitoring continues to be inexact, tedious, inefficient and costly. A method and system are still lacking which are capable of the most efficient and most accurate monitoring of corrosion products.

SUMMARY OF THE INVENTION

Accordingly, it is an object of the present invention to provide a corrosion product monitoring method and system capable of continuously and effectively monitoring corrosion products in, e.g., a nuclear power plant.

It is another object of the present invention to provide a corrosion product monitoring method and system, wherein large amounts of sample can be processed and accurately quantified over a short period of time.

It is another object of the present invention to provide a corrosion product monitoring method and system, wherein sample monitoring is performed at a constant flow rate and temperature.

It is another object of the present invention to provide a corrosion product monitoring method and system, wherein solid particulates greater than 0.2 micrometers in size can be separated and suspended relative to soluble and sub-colloidal corrosion products.

Finally, it is an object of the present invention to provide a corrosion product monitoring method and system, wherein the filter is inert and free of leachable contaminants.

To achieve the foregoing and other objects of the present invention, and in accordance with the purposes of the invention, there are provided the following method and system for monitoring corrosion products in a nuclear power plant.

The system is a recirculation loop including generally a sample inlet connection, a particulate collection vessel, a microporous "cross flow" filter, a recirculating pump and valves to control the flow rate. This system processes a representative sample taken via the sample line from, e.g., the secondary fluid system at a constant flow rate. The filter is previously filled with a known volume of deionized water. When a relatively short time has elapsed to stabilize conditions in the sample line, i.e., a trial run, an actual sample run is started by feeding sample to the particulate vessel. The sample is then introduced to the filter and returned to the particulate collection vessel by the recirculation pump. The solid particulates in the sample are separated and suspended in the filter. The accumulating particulate corrosion products are maintained as a concentrated suspension within the recirculation loop of the corrosion product system. The concentration of these particulates increases in the recirculation loop and particulate collection vessel as the actual sample run progresses. The permeate through the filter is passed to an ion exchange column (also previously filled with deionized water) to concentrate soluble ions. The filter is backwashed on a timed cycle by gas pressure or by water pressurized by a pump, after realigning the system valves. The total sample volume is determined by measuring the amount of filtered, deionized water discharged during the actual sample run, based on total weight, total flow or time at a constant discharge rate. At the end of the actual sample run a sample of the concentrated solid particulates is drawn directly from the particulate collection vessel for analysis. A concentration factor is then determined from the total sample volume divided by the initial system volume.

The related method includes the steps of: taking a sample from a fluid stream; introducing the sample to a recirculation loop system having an initial system volume; separating solid particulates from soluble corrosion products and suspending the solid particulates; collecting the solid particulates in a particulate collection vessel; and determining a corrosion concentration factor from the total sample volume divided by the initial system volume.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Figure 1:
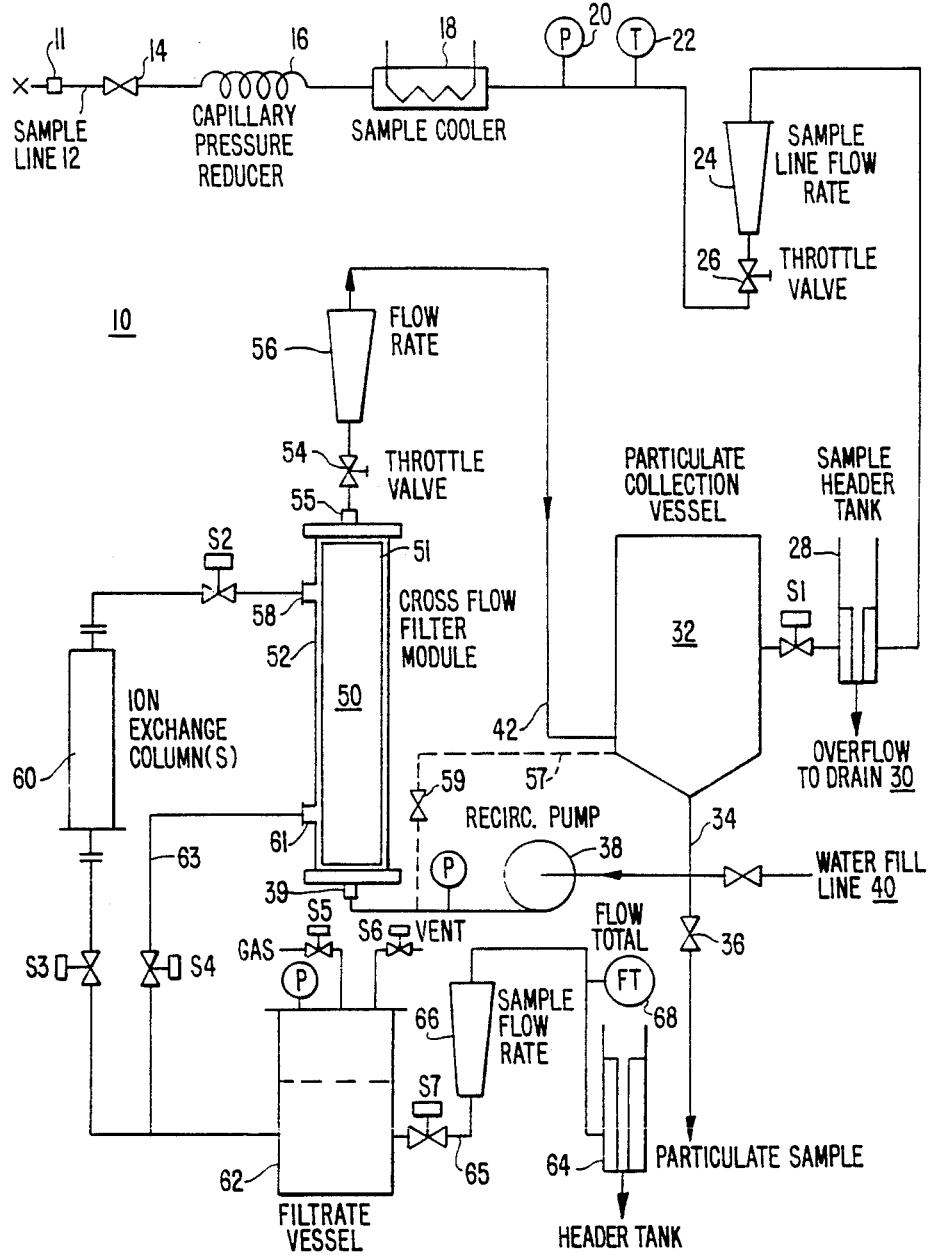
FIG. 1 is a schematic diagram illustrating the corrosion product monitoring method and system according to one embodiment of the present invention.

In order to overcome the above-discussed drawbacks related to conventional monitoring methods and systems, the present invention incorporates a "cross-flow" filter in a recirculation loop. The loop also includes a particulate collection vessel, a recirculating pump and valves to control the flow rate and pressure. Using this loop, the solid particulates can be separated from soluble components/contaminants in the fluid sample and maintained as a concentrated suspension during the actual sample run.

The cross-flow filter includes a module with a microporous, inert membrane through which water and soluble contaminants pass under moderate feed pressure and high feed velocity. Unlike reverse osmosis and ultrafiltration, the microporous membrane does not reject soluble contaminants such as salts, soluble metal hydroxides and organics of high molecular weights. The microporous membrane does prevent passage of colloidal and suspended solids of particle size greater than 0.1 to 10 microns depending on the membrane choice.

The soluble contaminants which pass through the porous membrane can be sampled directly, or concentrated on an adsorption column(s) using ion exchange resins or other adsorbents for later elution and analysis. The deposition of particulate solids on the filter membrane is minimized by the high fluid velocity and shear forces at the membrane surface. Periodically the membrane can be backwashed by reversing the flow through the membrane pores to remove any residual particulate solids built up during long term operation.

The system processes the representative sample at a constant flow rate and temperature. In this regard, a bypass is used in the sample line so that steady state flow through the sample line can be established for a trial run stabilization period before actual sampling. This period can be 24 hrs. for a central sampling point with several hundred feet of sample line, and 15 min. for a short, local, sample line.

When sufficient time has elapsed to stabilize conditions in the sample line, normally less than one hour for a local sample point, the actual sample run can be started by feeding sample into the recirculation loop system. The soluble contaminates pass through the filter and may be introduced to an ion exchange column to concentrate the soluble ions. The filter module and ion exchange column are previously filled with a known volume of deionized water. The solid particulates are suspended in the filter and the concentration thereof increases in the recirculation loop, particularly the filter and particulate collection vessel, as the actual sample run progresses.

The filter module is backwashed on a timed cycle by filtered water pressurized by gas pressure or a pump, by realigning the system valves. The backwash period is relatively short and will not affect the actual sample run. The total system volume is then determined by measuring the amount of filtered, deionized water discharged during the actual sample run. This can be done by total weight, total flow or time at a constant discharge rate. A concentration factor can be determined from the total sample volume divided by the initial system volume. At the end of the actual sample run, a sample of the concentrated solid particulates can be drawn from the particulate collection vessel for analysis.

This corrosion product monitoring system and method can rapidly process several hundred liters of sample over a period of only a few hours, instead of the conventional period of days. In addition, sampling can be performed at a constant flow rate, and solid particulates greater than 0.2 micrometers in size can be separated from soluble and sub-colloidal corrosion products. Further, the filter membrane is inert and free of leachable contaminants to avoid the above-discussed problems observed with conventional Millipore ® filter membranes.

More particularly, FIG. 1 schematically illustrates the corrosion product monitoring system 10 according to the present invention. This system can be used in a nuclear reactor corrosion product sampling program. U.S. Pat. No. 3,976,541 illustrates generally a nuclear reactor steam generator, and U.S. Pat. No. 4,472,354 illustrates sampling from the secondary fluid system of such a reactor.

A sample is taken at a local sample point X in the secondary system, such as the feedwater, condensate, heater drains or steam generator blowdown. The sample is removed by an isokinetic nozzle 11 connected to a sample line 12 including an isolation valve 14.

The sample line 12 material should be inert. Further, to minimize solid particulates deposition in the sample line, the sample should be in continuous turbulent flow with a minimum of restrictions. Finally, the sample line 12 should be as short as possible.

The sample should be depressurized and cooled relatively close to the sample point X. The pressure can be reduced by flow through a capillary pressure reducer 16 of the required length. A sample cooler 18 can be installed to reduce the temperature of the fluid from the operating range of about 500° to 600° F. to about 100° F. Secondary coolers are usually required with conventional monitoring systems to further reduce the temperature to the 72° F. required for chemistry instrumentation. However, secondary coolers are not required for the present invention.

Indicators are included in the sample line 12 for pressure 20, temperature 22 and flow rate 24. These indicators 20, 22, 24 are important for establishing steady state, trial run, sampling conditions in the sample line 12 prior to starting an actual sample run. A throttle valve 26 is located upstream of the flow rate indicator 24.

The sample flow is directed, via the sample line 12, to a sample header tank 28 including an overflow 30 to drain. The sample flow is maintained at a constant flow rate which is higher than the sampling rate.

After the trial run, sample flow is introduced from the sample header tank 28 to a particulate collection vessel 32 through a solenoid valve S1. The particulate vessel tank 32 has some freeboard to allow the level of fluid sample to rise during the backwash described below. The base of the particulate collection vessel 32 has an exit pipe 34 with connections to a particulate sample valve 36, a recirculating pump 38, and a valved water fill line 40. The pump 38 introduces sample to the filter 50 via an inlet 39. The particulate collection vessel 32 also includes a circulation return line 42 from the filter 50 to provide mixing.

As noted above, the filter 50 of the present invention incorporates a "cross-flow" filter module 51. Cross-flow filter modules are currently commercially available in different sizes, materials and configurations for other uses. The membranes thereof are available as flat sheets, plates, frames, wound spirals, hollow fibers or tubes. The preferred membrane configuration for the present invention is tubular, allowing solid particulate feed to the internal surface thereof. This configuration allows high shear forces to be maintained at the membrane surface and the module is easy to open for inspection and cleaning.

Other microporous membrane materials can be used for the filter of this invention. For high temperature cross-flow filtration, tubular microporous metals and ceramics can be used for corrosion product sampling of hot reactor coolant. Even though these membranes would lose some weight under the increased temperature, the loss would have a much less serious effect on the corrosion monitoring than the weight loss noted with conventional silver filters.

The preferred module 51 used with the filter 50 according to the present invention is a Microdyne ® MD 020 manufactured by Enka AG Product Group Membrana of West Germany and sold by Enka America, Inc. of Ashville, N.C. 28802. The membrane of this module 51 is a microporous plastic, i.e., tubular polypropylene with a pore size of 0.2 microns. Polypropylene is an inert polymer to most chemical solutions and is not readily contaminated by colloidal corrosion products. The module 51 has a 0.036 $m^2$. membrane area consisting of three tubes with a 5.5 $m^2$ internal diameter, an 8.6 $m^2$ outer diameter, and a 0.75 m length. The filter 50 also includes a module housing 52 and connections thereto described below, which are also constructed of polypropylene. The maximum temperature at the module 51 is 60° C. and maximum pressure drop over the membrane at 25° C. is 43.5 psi. for the feed mode and 29 psi. for the backwash mode. At the recommended fluid velocity through the tubes of 8 fps., the pressure drop is about 2 psi., so that feed recirculation can be obtained by a canned centrifugal pump 38 delivering 2.9 gpm. at 45 psig.

During recirculation, the feed flow rate and pressure from the filter 50 to the particulate collection vessel 32 can be regulated by a throttle valve 54 located at an outlet 55 of the filter 50. The feed flow rate is indicated by a flowmeter 56 placed upstream of the throttle valve 54.

If a pump 38 with a higher flow capacity is used, an additional throttle valve 59 can be placed on a line 57 bypassing the filter 50 to the particulate collection vessel 32, which would also provide additional mixing in the particulate collection vessel 32. The filtrate flow rate is about 2400 $l/m^2/h$. at a membrane pressure drop of 40 psi., so that a net sample flow rate of about 75 l/h. should be obtained with a single module 51.

The filter 50 has two connections on the side thereof. One is an outlet 58 for the permeate and is connected through a solenoid valve S2 to a small ion exchange column 60 used to concentrate soluble contaminants such as metal ions. The size of the ion exchange column 60 can be chosen based on the pH of the sample fluid. Another side outlet 61 leads via a line 63 to a filtrate vessel 62 described below. A solenoid valve S4 is incorporated in the line 63.

The effluent from the ion exchange column 60 is passed through a solenoid valve S3 into the filtrate vessel 62. The filtrate vessel 62 has a capacity of about 1 liter and acts as a reservoir of filtered water (filtrate) for backwashing the filter 50. The upper part of the filtrate vessel 62 has a pressure indicator, a solenoid valve S5 providing an inlet for gas to pressurize the filtered water for backwashing, and another solenoid valve S6 acting as an atmospheric vent valve. Normally the filtered water is discharged, through a line 65 and a solenoid valve S7, to a header tank 64 and overflows to drain. An indicating flowmeter 66 and a total flowmeter 68 are provided on the line 65 to measure the sample flow rate and the total sample volume, respectively.

On completion of the actual sample run, it is necessary to backwash the module 51 prior to sampling the particulate solids accumulated in the particulate collection vessel 32. After a period of the actual sample run, it may also be necessary to backwash to remove particulate solid deposits on the surface of the membrane which reduce the sample flow rate.

Backwashing is accomplished by pressurizing the filtrate vessel 62 via valve S5 with an inert gas at a pressure of about 25 psi. higher than the feed pressure. Solenoid valves S1, S2, S3, S6 and S7, which are normally open during the actual sample run, are closed and valves S4 and S5 are opened to allow the filtered water to enter the side of the filter 50 via outlet 61 under pressure, while isolating the sample inlet 39 and outlet 58. The reverse flow pulse of filtered water through the membrane pores dislodges any deposited particulate solids. A typical backwash cycle is about 15 seconds every half hour and requires about 0.2 l of filtrate.

At the completion of the backwash cycle solenoid valves S4 and S5 are closed and solenoid valves S2, S3 and S6 are opened. The pressurized gas in the filtrate vessel 62 is vented and the filtrate flow is resumed until normal levels are restored in the particulate collection vessel 32 and filtrate vessel 62. At this point solenoid valves S1 and S7 are opened to restore normal flow for the actual sample run.

As will be understood by one of average skill in the field, the operation of the trial and actual sample runs can be controlled automatically by a programmable controller (not shown). In this regard, automatic control equipment could be used to eliminate the requirement for manual setting of the throttle valve 26 to ensure a constant sample flow rate.

Figure 2:
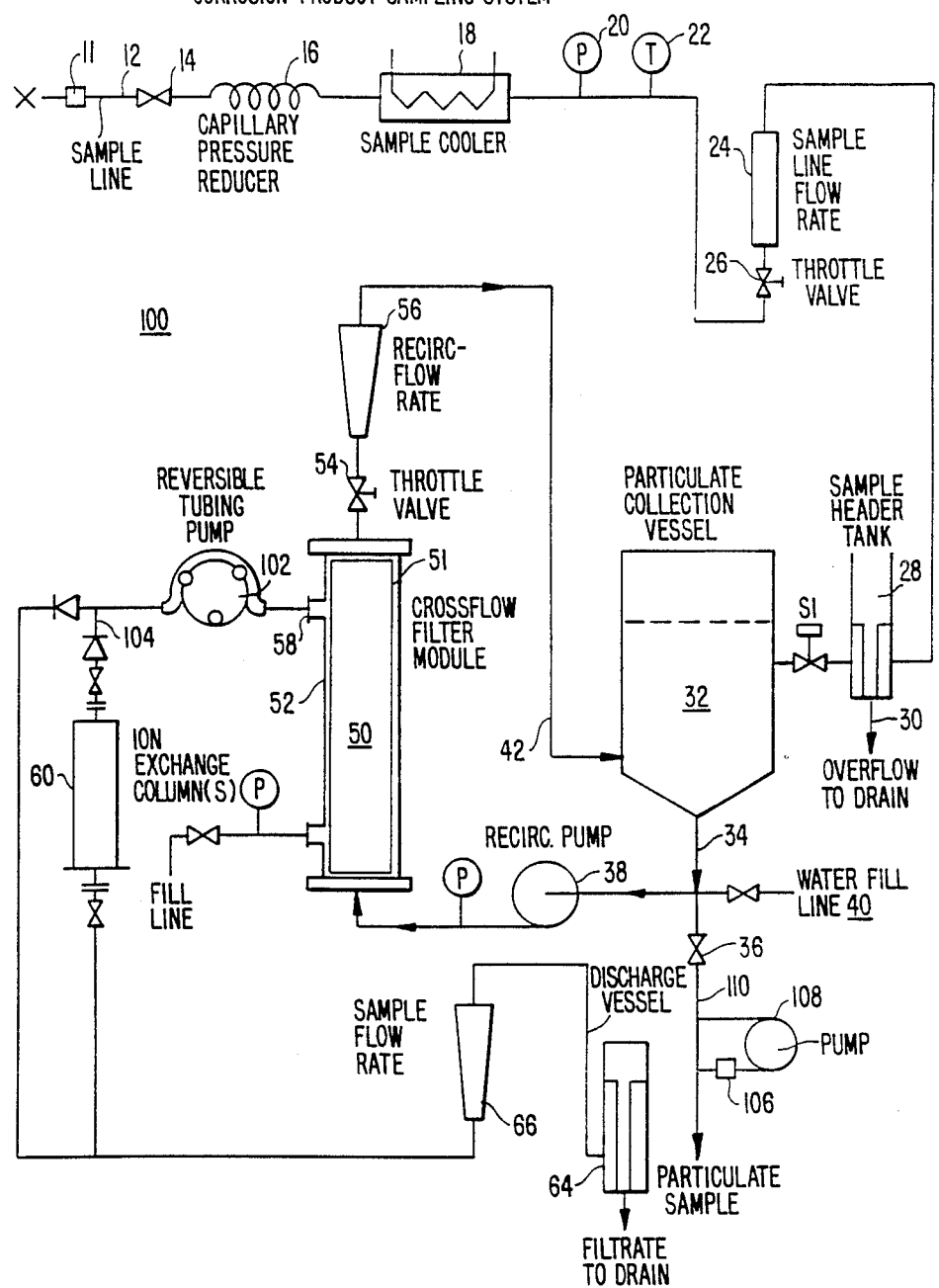
FIG. 2 is a schematic diagram illustrating the corrosion product monitoring method and system according to an alternate embodiment.

FIG. 2 shows an alternate embodiment of a corrosion monitor system 100 according to the present invention. In FIG. 2, members corresponding to those in FIG. 1 are referred to by the same reference numerals. The difference between the two embodiments is basically that a reversible tubing pump 102 is used for periodic backwash, instead of the pressurized filtrate vessel 62. The reversible tubing pump 102 is positioned between the outlet 58 of the filter 50 and a line 104 leading to the ion exchange column 60. As can be seen, the structure and control of this system 100 is simpler than the system 10, since the filtrate vessel 62 and the solenoid valves S2–S7 are eliminated.

The present invention can also be used as a continuous, in-line, monitoring system. In this regard, a continuous sample is taken from the particulate collection vessel 32 using the particulate sample valve 36. The concentration of corrosion products can be measured by a concentration monitoring device 106, such as a turbidity monitor, and the results recorded continuously. It is also possible to monitor particulate concentrations with a liquid particle counter, instead of the turbidity monitor. Monitoring concentration is useful for determining transients occurring during changes in plant operations and for monitoring the performance of condensate polishers or magnetic filters. The corrosion concentration factor is the ratio of the filtered water to the solid particulate sampling rate at the particulate sample valve 36.

An example of a suitable turbidity monitor is a Hach model 1720C low range turbidimeter. The cross-flow filtration module 51 acts as a particle concentrator on a continuous flow basis so that transients and long term trends in the particulate corrosion product concentration can be monitored and recorded.

More particularly, as shown in FIG. 2, the turbidity monitor 106 can be attached to a particulate sample line 110 via a positive displacement pump 108 supplying a flow rate between 15 and 30 l/h. The minimum detectable level of the turbidity monitor 106 is 0.002 NTU and the accuracy is 2% at turbidity values greater than 0.1 NTU. The turbidity monitor 106 has a response time of 5 minutes to 90% of full scale at a concentrated sample flow rate of 30 l/h. As 0.1 NTU represents approximately 100 ppb of particulate corrosion product, a concentration factor of about 50 times would be required to accurately monitor the corrosion product concentration, normally a few ppb, in feedwater of condensate. This requires a sample flow rate of 750 to 1500 l/h. which can be handled by a larger filter module 51 such as the Enka Microdyne ® MD 080 TP 2N with 1 m². filtration surface area. The other components of the system 100 will also be larger so as to be better suited for a permanently installed monitoring system. A corrosion product monitoring system incorporating a turbidity monitor is larger than the corrosion product sampling method described above and could be installed in a floor mounted cabinet.

The advantages of the present invention over conventional corrosion monitoring systems and methods are:

1. Constant flow rate sampling is attainable since permeation rate of soluble contaminants through the filter membrane is steady at constant applied temperature and pressure.

2. Much higher sample rates can be used, minimizing sample line deposition and time required to obtain a sufficient solid particulates sample for accurate analysis.

3. The solid particulates are retained as a concentrated suspension so that particle size determinations can be readily made.

4. The progress of the actual sample run for solid particulates can be monitored by turbidity measurements to record transients such as crud bursts.

5. Analysis of the accumulated solid particulates can be readily carried out by conventional methods available in the power plant laboratory.

6. Manual preparation and handling of the filter is not required, and specialized procedures to minimize fluid sample contamination are not necessary.

7. The system can be easily adapted for unattended operation using known automatic controls, allowing one technician to operate several sample points simultaneously.

8. Since samples can be taken in a relatively short time period, contemporaneously running in-plant experiments varying chemistry control parameters are feasible for obtaining comparative corrosion product transport data.

9. There are a wide variety of configurations, materials and pore sizes available for the microporous membrane, for both high and low temperature sampling, and for primary and secondary system applications.

10. Cleaning of the cross-flow filter module can normally be done by periodic backwashing, however, it is also feasible to clean or decontaminate chemically as the materials are inert.

The foregoing is considered illustrative only of the principles of the invention. For example, although the present invention has been described in particular relation with a nuclear power plant, same can be used in a fossil fueled power plant, or any fluid system where corrosion product monitoring is required. In addition, although a single sampling point and recirculation loop for a secondary fluid system, are shown and described, a plurality of points and loops can be incorporated in a single power plant, as desired, in either the primary or secondary fluid systems.

Further, since numerous modifications and changes will readily occur to those skilled in the art, it is not desired to limit the invention to the exact construction and operation shown and described. Accordingly, all suitable modifications and equivalents may be resorted to, falling within the scope of the invention and the appended claims and their equivalents.

I claim as my invention:

1. A system for monitoring non-soluble particulates separated from soluble components in a fluid system, comprising:
    (a) means for sampling the fluid system of a nuclear power generator;
    (b) a particulate collection vessel in fluid communication with the sampling means via a sample line;
    (c) means, in fluid communication with the particulate collection vessel via a recirculation loop, for separating the soluble components from the non-soluble particulates and suspending the non-soluble particulates;
    wherein the suspended non-soluble particulates are accumulated during operation of the recirculation loop in the particulate collection vessel; and
    (d) means, in fluid communication with the particulate collection vessel, for detecting concentration of the suspended non-soluble particulates.

2. The system as recited in claim 1, wherein the separating means is an inert, microporous, cross-flow, filter.

3. The system as recited in claim 2, wherein the filter includes a filter module configured in a shape selected from the group consisting of a flat sheet, a plate, a frame, a spiral, hollow fibers and a tube.

4. The system as recited in claim 1, wherein the fluid system sampled is a secondary fluid system of a nuclear power plant.

5. The system as recited in claim 1, wherein the suspended, non-soluble particulates are greater than 0.2μ in size.

6. The system as recited in claim 1, wherein the particulate collection vessel includes a non-soluble particulates discharge.

7. A system for separating soluble components from non-soluble particulates in a fluid system, comprising:
 (a) means for sampling the fluid system:
 (b) a particulate collection vessel in fluid communication with the sampling means via a sample line;
 (c) means, in fluid communication with the particulate collection vessel via a recirculation loop, for separating the soluble components from the non-soluble particulates and suspending the non-soluble particulates; and
 (d) ion exchange means, in fluid communication with the separating means, for receiving and concentrating the separated soluble components,
 wherein the suspended non-soluble particulates are accumulated during operation of tube recirculation loop in the particulate collection vessel.

8. The system as recited in claim 7, further comprising:
 (e) means for backwashing the separating means.

9. The system as recited in claim 8, wherein the backwashing means comprises:
 a pressurized filtrate vessel in fluid communication with the separating means.

10. The system as recited in claim 8, wherein the backwashing means comprises:
 a reversible pump in fluid communication with the separating means.

11. A system for separating soluble components from non-soluble particulates in a fluid system, comprising:
 (a) means for sampling the fluid system;
 (b) a particulate collection vessel in fluid communication with the sampling means via a sample line;
 (c) means, in fluid communication with the particulate collection vessel via a recirculation loop, for separating the soluble components from the non-soluble particulates and suspending the non-soluble particulates;
 (d) means, selected from the group consisting of a turbidity monitor and a liquid particle counter, for monitoring concentration of the non-soluble particulates, in fluid communication with the particulate collection vessel,
 wherein the suspended non-soluble particulates are accumulated during operation of the recirculation loop in the particulate collection vessel.

12. A system for separating soluble components from non-soluble particulates in a fluid system, comprising:
 (a) means for sampling the fluid system;
 (b) a particulate collection vessel in fluid communication with the sampling means via a sample line; and
 (c) means in fluid communication with the particulate collection vessel via a recirculation loop, for separating the soluble components from the non-soluble particulates and suspending the non-soluble particulates;
 wherein the suspended non-soluble particulates are accumulated during operation of the recirculation loop in the particulate collection vessel,
 wherein the separating means is an inert, microporous, cross-flow filter,
 wherein the filter includes a filter module configured in a shape selected from the group consisting of a flat sheet, a plate, a frame, a spiral, hollow fibers and a tube, and
 wherein the filter module is made from a material selected from the group consisting of microporous plastic, inorganic metal or ceramic.

13. A system for separating soluble components from non-soluble particulates in a secondary fluid system of a power plant, comprising:
 (a) means for sampling the secondary fluid system;
 (b) a particulate collection vessel in fluid communication with the sampling means via a sample line;
 (c) a microporous, cross-flow filter, in fluid communication with the particulate collection vessel via a recirculation loop, for separating the soluble components from the non-soluble particulates and suspending the non-soluble particulates,
 wherein the suspended non-soluble particulates are accumulated during operation of the recirculation loop in the particulate collection vessel;
 (d) ion exchange means in fluid communication with the filter, for receiving and concentrating the separated soluble components; and
 (e) means for backwashing the filter.

* * * * *